US00PP17835P2

(12) United States Plant Patent
Fischer-Töhl

(10) Patent No.: US PP17,835 P2
(45) Date of Patent: Jun. 26, 2007

(54) ***GERANIUM* PLANT NAMED 'BALSHOROZLE'**

(50) Latin Name: *Pelargonium×hortorum*
Varietal Denomination: Balshorozle

(75) Inventor: Ilse Fischer-Töhl, Kirchlinteln (DE)

(73) Assignee: Silze GmbH & Company KG, Weener (DE)

( * ) Notice: Subject to any disclaimer, the term of this patent is extended or adjusted under 35 U.S.C. 154(b) by 0 days.

(21) Appl. No.: 11/272,364

(22) Filed: Nov. 10, 2005

(51) Int. Cl.
*A01H 5/00* (2006.01)

(52) U.S. Cl. ..... Plt./328
(58) Field of Classification Search ..... Plt./328, Plt./329, 325, 330
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Geranium* plant named 'Balshorozle' characterized by its semi-double pink-colored flowers with dark pink-colored spots, dark green-colored foliage, and moderately vigorous, upright growth habit.

1 Drawing Sheet

Latin name of genus and species of plant claimed: *Pelargonium×hortorum.*
Variety denomination: 'Balshorozle'.

BACKGROUND OF THE INVENTION

The present invention relates to a new and distinct cultivar of *Geranium* plant botanically known as *Pelargonium×hortorum* and hereinafter referred to by the cultivar name 'Balshorozle'.

The new cultivar originated in a controlled breeding program in Weener, Niedersachen (Northern Germany) during the summer of 1999. The objective of the breeding program was the development of *Geranium* cultivars that have unique flower colors, dark green-colored foliage, and vigorous, upright mounded growth habits.

The female (seed) parent of the new cultivar was 'Klemiga', U.S. Plant Pat. No. 9,205, characterized by its neon pink-colored flowers, grey green-colored foliage, and upright, compact growth habit. The male (pollen) parent of the new cultivar was 'BFP-1705', U.S. Plant Pat. No. 11,396, characterized by its semi-double salmon and light pink-bicolored flowers, dark green colored-foliage, and vigorous, upright growth habit. The new *Geranium* was discovered and selected by the inventor as a single flowering plant within the progeny of the above stated cross-pollination during June 2000 in a controlled environment at Weener, Niedersachen (Northern Germany).

Asexual reproduction of the new cultivar by terminal stem cuttings since June 2000 at Arroyo Grande, Calif. and West Chicago, Ill. has demonstrated that the new cultivar reproduces true to type with all characteristics, as herein described, firmly fixed and retained through successive generation of such asexual propagation.

SUMMARY OF THE INVENTION

The following characteristics of the new cultivar have been repeatedly observed and can be used to distinguish 'Balshorozle' as a new and distinct cultivar of *Geranium* plant:

1. Semi-double pink-colored flowers with dark pink-colored spots;
2. Dark green-colored foliage; and
3. Moderately vigorous, upright growth habit.

Plants of the new cultivar differ from plants of the female parent primarily in flower color and foliage color and from plants of the male parent primarily in flower color and plant vigor.

Of the many commercially available *Geranium* cultivars known to the inventor, the most similar in comparison to the new cultivar is 'Fip 469', U.S. Plant Pat. No. 15,379. However, in side by side comparisons, plants of the new cultivar differ from plants of 'Fip 469' in the following characteristics:

1. Plants of the new cultivar are more compact than plants of 'Fip 469'; and
2. Plants of the new cultivar have a different flower color from plants of 'Fip 469'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balshorozle'. The plants were grown in 10 cm pots for 9 weeks in a greenhouse at West Chicago, Ill.

DETAILED BOTANICAL DESCRIPTION

Figure 1:
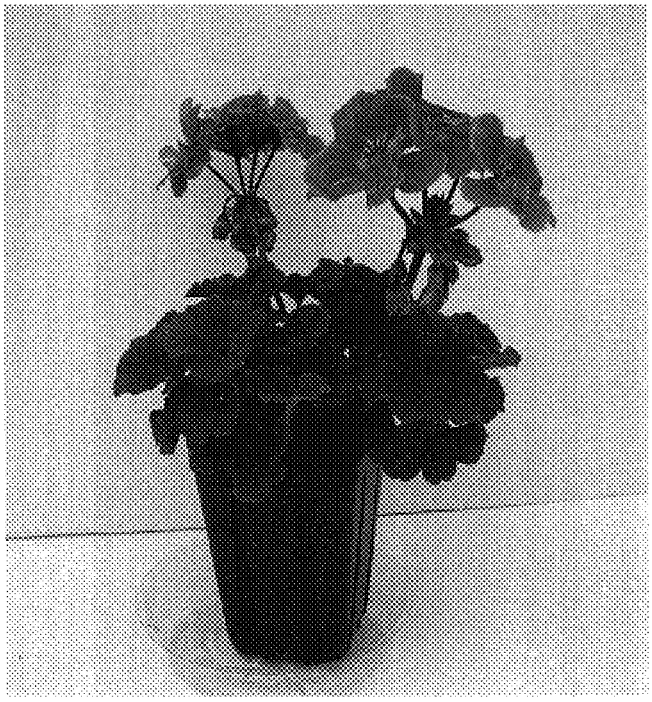
FIG. 1 illustrates a side view of the overall growth and flowering habit of 'Balshorozle'.
Figure 2:
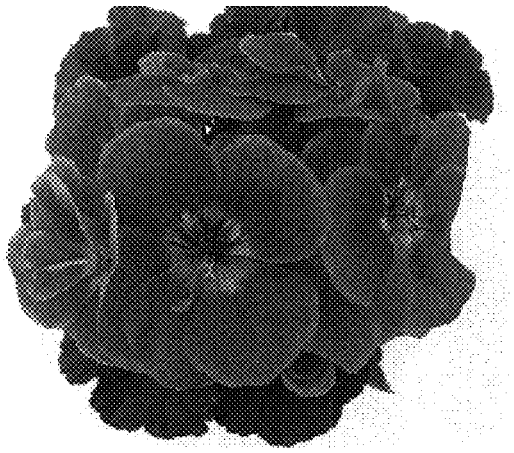
FIG. 2 illustrates a close-up view of a single umbel of 'Balshorozle'.
Figure 3:
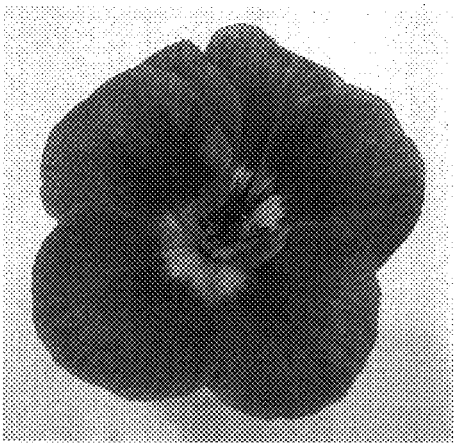
FIG. 3 illustrates a close-up view of a single flower of 'Balshorozle'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 19, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 9 weeks utilizing a soilless growth medium. Greenhouse temperatures were maintained at approximately 65° F. to 75° F. (18° C. to 24° C.) during the day and approximately 62° F. to 68° F. (17° C. to 20° C.) during the night. Greenhouse light levels of 3,500 to 6,000 footcandles were maintained during the day.

Botanical classification: *Pelargonium×hortorum* cultivar Balshorozle.

Parentage:

*Female parent.*—'Klemiga', U.S. Plant Pat. No. 9,205.

*Male parent.*—'BFP-1750', U.S. Plant Pat. No. 11,396.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 9 weeks from a rooted cutting.

*Growth habit and general appearance.*—Moderately vigorous and upright.

*Size.*—Height from soil level to top of plant plane: Approximately 18.2 cm. Height from soil level to top of foliage: Approximately 10.4 cm. Width: Approximately 21.2 cm.

*Branching habit.*—Freely basal branching. Approximately 3 branches per plant.

*Branch.*—Strength: Strong. Length: Approximately 5.6 cm. Diameter: Approximately 6.6 mm. Texture: Densely pubescent with short, soft hairs. Color: Closest to 143C. Internode length at center of branch: Approximately 1.2 cm.

*Foliage.*—Number of leaves per lateral branch: Approximately 12. Fragrance: None. Form: Simple. Arrangement: Opposite. Aspect: Petiole is at acute angle to stem and blade is at a right angle to stem. Shape: Reniform. Margin: Crenate. Apex: Rounded. Base: Cordate. Venation pattern: Palmate. Length of mature leaf: Approximately 4.6 cm. Width of mature leaf: Approximately 7.6 cm. Texture of upper and lower surfaces: Densely pubescent with short, soft hairs. Color of upper surface of mature foliage: Darker than 137A with venation of 144B. Color of lower surface of mature foliage: 137C with venation of 144B. Petiole length: Approximately 5.0 cm. Petiole diameter: Approximately 3.0 mm. Petiole texture: Densely pubescent with short, soft hairs on both upper and lower surfaces. Petiole color: Closest to 137C.

Flowering description:

*Flowering habit.*—'Balshorozle' is freely flowering under outdoor growing conditions with substantially continuous blooming from spring through autumn and year round in greenhouse environment.

*Time to first flower.*—Approximately 10.5 weeks from sticking of unrooted cutting.

*Lastingness of individual bloom.*—Approximately 5 to 7 days.

Inflorescence description:

*Type.*—Hemispherical umbel. Position: Above foliage. Number of open umbels per plant at nine weeks: Approximately 1. Number of developing umbels per plant at nine weeks: Approximately 2. Umbel diameter: Approximately 11.8 cm. Umbel height/depth: Approximately 7.1 cm. Number of flowers per umbel: Approximately 10. Fragrance: None.

*Peduncle.*—Strength: Strong. Aspect: Erect. Length: Approximately 9.5 cm. Diameter: Approximately 3.5 mm. Texture: Densely pubescent with short, soft hairs. Color: 144A.

Flower description:

*Bud rate of opening.*—Generally takes 3 to 5 days for bud to progress from first color to fully open flower.

*Bud just before opening.*—Shape: Elliptic. Length: Approximately 1.9 cm. Diameter: Approximately 1.0 cm. Color of petals: N57A. Texture: Sepals are pubescent and petals are glabrous.

*Corolla.*—Form: Semi-double. Shape: Round. Diameter: Approximately 5.7 cm. Depth: Approximately 2.0 cm.

*Petals/petaloids.*—Quantity: Approximately 8 petals and 4 irregular shaped petaloids per flower. Appearance: Dull, velvety. Aspect: Downward turning at margin. Arrangement: Imbricate. Shape: Obovate. Apex: Obtuse. Base: Attenuate. Margin: Entire. Texture of upper and lower surfaces: Glabrous. Length of upper petal: Approximately 3.2 cm. Width of upper petal: Approximately 2.3 cm. Length of lower petal: Approximately 3.1 cm. Width of lower petal: 2.5 cm. Color of upper surface of upper petal: Background of 72C with mottling of N57B; large sized spot in center closest to 46B with 73D and venation of 60B at base. Mottling is less intense and often absent from the margin area. Color of lower surface of upper petal: 73D with venation of 73A. Color of upper surface of lower petal: Background of 72C with mottling of N57B; medium sized spot in center closest to 46B with 73D and venation of 60B at base. Mottling is less intense and often absent from the margin area. Color of lower surface of lower petal: 73D with venation of 73A.

*Pedicel.*—Strength: Strong. Angle: Acute. Length: Approximately 4.1 cm. Diameter: Approximately 1.7 mm. Texture: Densely pubescent with short, soft hairs. Color: 144A with overlay of 185A.

*Calyx.*—Shape: Five-pointed star. Width: Approximately 1.9 cm.

*Sepals.*—Quantity per flower: 5. Shape: Lanceolate. Apex: Acuminate. Margin: Entire. Length of upper sepal: Approximately 1.5 cm. Width of upper sepal: Approximately 4.8 mm. Length of lower sepal: Approximately 1.4 cm. Width of lower sepal: Approximately 3.2 mm. Texture of upper surface: Glabrous. Texture of lower surface: Densely pubescent with long, soft hairs. Color of upper and lower surfaces: 144A with venation and base of 185A.

*Reproductive organs.*—Androecium: Quantity of mature anthers: Approximately 3 to 5 per flower. Anther shape: Oblong. Anther length: Approximately 2.0 mm. Anther color: 72A. Filament length: Approximately 6.0 mm. Filament color: 155D. Pollen amount: Abundant. Pollen color N163A. Gynoecium: Pistil quantity: One per flower. Pistil length: Approximately 1.2 cm. Stigma shape: Five-branched. Stigma length: Approximately 3.0 mm. Stigma color: 61B. Style length: Approximately 2.8 mm. Style color: 61B. Ovary length: Approximately 6.1 mm. Ovary texture: Sericeous. Ovary color: 144C.

Seed and fruit production: Neither seed not fruit production has been observed.

Disease and pest resistance: Resistance to pathogens and pests common to *Geranium* has not been observed.

What is claimed is:

1. A new and distinct cultivar of *Geranium* plant named 'Balshorozle', substantially as herein shown and described.

* * * * *